United States Patent [19]
Hayes

[11] Patent Number: 5,012,052
[45] Date of Patent: Apr. 30, 1991

[54] ISOTOPE-RATIO-MONITORING GAS CHROMATOGRAPHY-MASS SPECTROMETRY APPARATUS AND METHOD

[75] Inventor: John M. Hayes, Bloomington, Ind.

[73] Assignee: Indiana University Foundation, Bloomington, Ind.

[21] Appl. No.: 173,297

[22] Filed: Mar. 22, 1988

[51] Int. Cl.$^5$ .............................................. H01J 49/26
[52] U.S. Cl. ..................................... 250/288; 250/282
[58] Field of Search ................... 250/288, 288 A, 282; 73/23.1; 260/687 R

[56] References Cited

U.S. PATENT DOCUMENTS 3,638,396  2/1972  Lovelock ............................. 73/23.1
4,517,461  5/1985  Crandall ......................... 250/288 A

OTHER PUBLICATIONS

Matthews, D. E., "Isotope Ratio Determinations using Gas Chromatography-Mass Spectrometry", Ph.D. Dissertation, Dept. of Chemistry, Indiana University 1977.
Matthews, D. E. and Hayes, J. M., "Isotope-Ratio-Monitoring Gas Chromatograph Mass Spectrometry", *Analytical Chemistry*, vol. 50, p. 1456, Sep. 1978.
Sano, M. Yotsui, Y., Abe, H., Sasaki, S., "A New Technique for the Detection of Metabolities Labelled by the Isotope $^{13}$C Using Mass Fragmentography", *Biomed. Mass Spec.*, vol. 3, pp. 1-3, 1976.
Simonds, P. G., Shoemake, G. R., Lovelock, J. E., "Palladium-Hydrogen System", *Anal. Chem.*, vol. 42, No. 8, pp. 881-885, Jul. 1970.
Lovelock, J. E., Simmonds, P. G., Shoemake, G. R., "The Palladium Generator-Separator—A Combined Electrolytic Source and Sink for Hydrogen in Closed Circuit Gas Chromatography", *Analytical Chemistry*. vol. 42, No. 9, pp. 969-973, Aug. 1970.
Dencker, W. D., Rushneck, D. R., Shoemake, G. R., "Electrochemical Cell as a Gas Chromatograph—Mass Spectrometer Interface", *Anal. Chem.*, vol. 44, No. 11, pp. 1753-1758, Sep. 1972.
Barrie, A., Bricout, J., Koziet, J., "Gas Chromatography—Stable Isotope Ratio Analysis at Natural Abundance levels", *Biomed. Mass Spec.*, vol. 11, No. 11, pp. 583-588, 1984.
Preston, T., Owens, N. J. P., "Preliminary $^{13}$C Measurments Using a Gas Chromatography Interfaced to an Isotope Ratio Mass Spectrometer", *Biomed. Mass Spec.*, vol. 12, No. 9, pp. 510-513, 1985.
Preston, T., Owens, N. J. P., "Interfacing an Automatic Elemental Analyzer with an Isotope Ratio Mass Spectrometer: the Potential for Fully Automated Total Nitrogen and Nitrogen-15 Analysis", *Analyst*, vol. 108, pp. 971-977, Aug. 198.
Gilmour, I., Swart, P. K., Pillinger, C. T., "The Carbon Isotopic Composition of Individual Petroleum Lipids", *Org. Geochem.*, vol. 6, pp. 665-670, 1984.

(List continued on next page.)

*Primary Examiner*—Bruce C. Anderson
*Attorney, Agent, or Firm*—Kirkland & Ellis

[57] ABSTRACT

An isotope-ratio-monitoring gas chromatography-mass spectrometry apparatus and method are disclosed which provide for on-line analysis of isotope compositions with high precision. With the apparatus and method, samples are introduced in a hydrogen carrier gas into a gas chromatograph and resolved into discrete compounds. The discrete compounds are thereafter introduced to a selectively permeable membrane separator, empolying palladium, palladium alloy or other suitable material, to separate out the hydrogen carrier. A replacement carrier gas is simultaneously introduced to carry the chromatographic sample to a combustion reactor, water separator and isotope-ratio-monitoring mass spectrometer. The replacement carrier gas is introduced at a lower flowrate than the hydrogen carrier gas, thus permitting lower flowrates to be introduced to the mass spectrometer to improve its precision. Flowrates to the mass spectrometer are thus reduced without any loss or fractionation of the sample. An improved combustion system is employed to reduce system volume and equalize system pressure, while still providing quantitative combustion.

22 Claims, 6 Drawing Sheets

OTHER PUBLICATIONS

Hut, G., Begemann, M. J. S., Weerkamp, H. R., "Determination of Isotope Ratios in the Natural Gas Components $CH_4$ and $N_2$ Separated by Gas Chromatography", *Isotope Geoscience*, vol. 2, pp. 75-83, 1984.

Welte, D. H., "Determination of $C^{13}/C^{12}$ Isotope Ratios of Individual Higher n-Paraffins from Different Petroleums", *Adavances in Organic Geochemistry* 19 pp. 269-277. Pergamon 1969.

Simmonds, P. G., Kerns, E., "Direct Aqueous Injection Gas Chromatography for the Analysis of Trace Organics in Water", *Journal of Chromatography*, vol. 186 pp. 785-794, 1979.

Piell, J. D., Oliver, K. D., McClenny, W. A., "Enhanced Performance of Nafion Dryers in Removing Water from Air Samples Prior to Gas Chromatographic Analysis", *Japca*, vol. 37, pp. 244-248, 1987.

Lopez, M., Kipling, B., Yeager, H. L., "Exchange Rates and Water Content of a Cation Exchange Membrane in Aprotic Solvents", *Anal. Chem.*, vol. 48, No. 8, pp. 1120-1122, 1976.

Volger, E. A., Meyers, P. A., Moore, W. A., "Comparison of Michigan Basin Crude Oils", *Geochim. Cosmochim.*, vol. 45, pp. 2287-2293, 1981.

Des Marais, D. J., Mitchell, J. M., Meinschein, W. G., Hayes, J. M., "The Carbon Isotope Biogeochemistry of the Individual Hydrocarbons in Bat Guano and the Ecology of the Insectivorous Bats in the Region of Carlsbad, New Mexico", *Geochimical Cosmochim.*, vol. 44, pp. 2075-2086, 1980.

Sweeley, C. C., Elliot, W. H., Fries, I., Ryhage, R., "Mass Spectrometric Determination of Unresolved Components in Gas Chromatographic Effluents", *Anal. Chem.*, vol. 38, No. 11, pp. 1549-1453, 1966.

Klein, P. D., Haumann, J. R., Eisler, W. J., "Gas Chromatograph—Mass Specrometer Accelerating Voltage Alternator System for the Measurement of Stable Isotope Ratios in Organic Molecules", *Anal. Chem.*, vol 44, No. 3, pp. 490-493, Mar. 1972.

Klein, P. D., Haumann, J. R., Hachey, D. L., "Stable Isotope Ratiometer—Multip Ion Detector Unit for Quantitative and Qualitative Stable Isotope Studies by Gas Chromatography—Mass Spectrometry", *Clin. Chem.*, vol. 21, No. 9, pp. 1253-1257, 1975.

Holland, J. F., Sweeley, C. C., Thrush, R. E., Teets, R. E., Bieber, M. A., "On-Line Computer Controlled Multiple Ion Detection in Combined Gas Chromatography—Mass Spectrometry", *Anal. Chem.*, vol. 45, No. 2, pp. 308-314, Feb. 1973.

Caprioli, R. M., Fies, W. F., Story, M. S., "Direct Analysis of Stable Isotopes with a Quadruple Mass Spectrometer", *Anal. Chem.*, vol. 46, No. 4, pp. 453-462, Apr. 1974.

Poster Exhibited by Applicant at a conference of the Geological Society of America in 1986.

"Gas Chromotography-Isotope Ratio Mass Spectrometer", Brochure for isochre II by VG Isogas, Ltd.

Freedman, P. A., Gillyon, E. C. P., Jumeau, E. J., "Design and Application of New Instrument for GC-Isotope Ratio MS", *American laboratory*, Jun. 1988, p. 114.

Brand, W. A. Ricci, M. P., and Habfast, K., "On-Line Combustion and High Precision Isotope Ratio Monitoring of Organic Compounds", Abstract, *11th International Mass Spectrometry Conference*, Bordeaux, 29 Aug.-2 Sep. 1988.

ISOTOPE-RATIO-MONITORING GAS CHROMATOGRAPHY-MASS SPECTROMETRY APPARATUS AND METHOD

FIELD OF THE INVENTION

The present invention relates to an apparatus and method for monitoring isotope ratios, such as carbon isotopes in natural abundances as present in sedimentary organic matter, fossil fuels and other organic and geological specimens, or in artificially enhanced abundances as found in labelled biomedical samples. More specifically, the present invention relates to improvements in isotope-ratio-monitoring gas chromatography - mass spectrometry (irm-GCMS) apparatus and methods which simplify isotope ratio monitoring, without compromising the precision heretofore only obtainable by much more time consuming prior art apparatus and methods requiring the introduction of substantially greater amounts of sample.

BACKGROUND OF THE INVENTION

It has been appreciated for some time that isotopic analysis of compounds provides a wealth of information extending beyond traditional structural chemical analyses. While quantitative and qualitative structural analyses identify the chemical composition of a compound or of individual molecules, isotopic analysis provides still further information concerning the source, origin and formation of such compounds and molecules.

In the field of geochemical oil exploration and prospecting, measurement of the isotopic compositions of large numbers of individual organic compounds of oil samples from various oil reservoirs assists in clarifying the origins of specific compounds, correlating the organic compounds with particular sources, recognizing the existence of multiple sources, examining the mechanisms of petroleum generation and improving the sensitivity of petroleum migration studies. This information, particularly in connection with seismic data, can be used to predict locations of other oil reservoirs to which oil may have migrated from a common source of generation or formation.

Isotope ratio monitoring has further applications in the biomedical field, wherein non-radioactive, stable isotopes are used as tracer labels in drug metabolism and other biomedical studies and where natural variations in isotopic abundances may also carry additional information regarding sources and fates of metabolites. Current non-radioactive, stable isotopic labelling apparatus and methods in the medical field employ costly labelled compounds having isotope ratios much greater than those found in natural abundance. Improvements in isotope ratio monitoring sensitivity and precision and a reduction in the size of required samples and in the time and complexity of isotopic analyses, however, will enhance applications in the biomedical field for non-radioactive, stable isotope ratio monitoring apparatus and methods.

Additional applications lie within the environmental sciences. Even though a pollutant may have several potential sources, it may happen that its isotopic composition will match that of only one of them, thus clearly identifying the source. In other cases, it may happen that a pollutant has an isotopic composition intermediate between those of two possible sources, thus allowing determination of the importance of each source.

Isotopic analysis is used to determine the relative abundance of various isotopes in a sample compound. In analyses of carbon isotopes, for example, the ratio of $^{13}C$ to $^{12}C$ in a sample compound is determined. Such ratio is typically compared or normalized with that of a known compound or standard. Several prior art methods and apparatus have been used in an effort to automate isotopic analysis of sample compounds. Each such method suffers from at least one of several deficiencies, which include, among other things, the labor intensity and substantial time required to perform the analysis, a lack of precision in the results, and requirements for large volumes of sample to perform the analysis.

In a first category of prior art methods and apparatus, commonly referred to as selected ion monitoring gas chromatography-mass spectrometry (SIM-GCMS), a gas chromatograph is directly connected to a single collector mass spectrometer of the type typically used for organic analysis (e.g., a magnetic sector or quadrupole mass spectrometer). The compound to be analysed is purified by elution from the gas chromatograph (or by other conventional means) and is introduced as intact molecules into the mass spectrometer ion source. The mass spectrometer fragments the compound in accordance with a known and expected pattern and the single detector is employed to ascertain the relative abundances of fragment ions at varying masses. Isotopic abundances of the sample compound are distinguishable from the mass spectrometer data based upon the differences in ion current intensities at the selected masses.

The SIM-GCMS apparatus and methods advantageously require only relatively small sample amount (picomoles to nanomoles). Moreover, because the entire analysis is done in a continuous, uninterrupted, automated sequence (i.e., "on-line"), the procedure is relatively uncomplicated, requiring minimal time and human intervention.

The above-noted advantages, however, are achieved at the expense of precision. Specifically, since the ion source of the mass spectrometer must be arranged so that thermal degradation of organic molecules is minimized, molecular residence times are brief and, as a result, efficiencies of ionization are often low. Ion currents are commonly in the range $10^{-11}$ to $10^{-15}$ amperes, and theoretical maximum precisions of ratio measurement (within the time of a gas chromatographic peak) are often only a few percent. Further, since a single detector is used to monitor the ion currents both $^{12}C$ and $^{13}C$ isotopic abundances, it must have a linear response for the range of abundances of both. Scanning with a single detector during the course of a chromatographic peak introduces systematic errors into the isotopic ratio determination. Although attempts been made to correct for such errors by altering the scan pattern (e.g., by adopting a unidirectional scan pattern), all such corrections are based upon the uncertain assumption that no fractionation occurs across the chromatographic peak for the eluted composition, i.e., that the compound is homogenous throughout the chromatographic peak.

Also, precision losses in SIM-GCMS apparatus and methods stem from the introduction of relatively large and complex molecules into the mass spectrometer directly as they are eluted from the gas chromatograph. The size of these molecules demands higher resolution from the mass spectrometer. The inevitable presence of the element hydrogen creates a situation in which loss or transfer (i.e., between molecular fragments) of hydrogen can produce a mass change of only one mass unit, exactly that associated with the presence or absence of a single carbon- or nitrogen-isotopic label. For example, an ion thought to contain an isotopic label may instead have picked up an extra hydrogen atom during fragmentation. An ion that has unexpectedly lost a hydrogen atom may be mistakenly identified as one that does not contain an isotopic label. Furthermore, as noted above, the molecules fragment in the ion source of the mass spectrometer which decreases the intensity of parent ions and complicates isotopic analysis and corrections for abundances of non-carbon isotopes (e.g., $^2H$ and $^{17}O$). Furthermore, the extent of fractionation between isotopes of the parent ion in the fragmentation process is unknown. It is thus not known whether one isotope will tend to fragment from the parent ion more often than another isotope, introducing still further possible errors in the measurement of the relative ratios of isotopes.

Because of the poor precision of SIM-GCMS techniques (e.g., 0.5 to 10.0%, depending upon conditions), their application to isotope monitoring have generally been limited to the detection of artificially labelled compounds having $^{13}C$ abundances substantially greater than the natural $^{13}C$ abundance in organic compounds.

The precision limitations of SIM-GCMS techniques led to isotopic analysis methods in which compounds are quantitatively combusted after being resolved by the gas chromatograph and before introduction into the mass spectrometer. Such combustion converts the carbon in the larger organic molecules to $^{12}CO_2$ and $^{13}CO_2$, which can then be analyzed with far greater efficiency. Because $CO_2$ is a small molecule containing only carbon and oxygen, fragmentation is minimized, problems of hydrogen transfer and loss are nonexistent, and calculation of carbon isotopic abundances from observed ion currents can be accomplished with far less uncertainty. Two general prior art approaches involving combustion of the effluent from a gas chromatograph before introduction into a mass spectrometer have been employed.

In a first such prior art approach, commonly referred to as the "off-line" approach, compounds are chromatographically separated and isolated, and thereafter separately analysed in a mass spectrometer. In one category of off-line apparatus and methods, the compounds eluted from the chromatographic column are individually collected and, thereafter, in a separate step, converted to $CO_2$ by combustion, e.g., in a quartz container. Isotopic analysis is thereafter performed on the collected combustion product, which includes both $^{12}CO_2$ and $^{13}CO_2$.

In another category of off-line apparatus and methods, the chromatographic effluent is combusted immediately upon exit from the gas chromatograph, and the products of combustion, containing $^{12}CO_2$ and $^{13}CO_2$, are collected, purified, and packaged in individual containers for further analysis.

In both categories of off-line apparatus and methods, the samples are individually transferred to a mass spectrometer (preferably a dual inlet, dual (or triple) collector isotope-ratio-monitoring mass spectrometer) and analysed in a conventional manner. These apparatus and methods yield very good precision (better than 0.1% relative standard deviation). However, because sample purification and sample combustion are performed off-line, the process is labor intensive and time consuming. Moreover, large quantities of sample (of the order of micromoles) are required.

In an attempt to overcome the disadvantages inherent in off-line isotopic analysis apparatus and methods, on-line approaches have been attempted, wherein the effluent from a gas chromatograph is introduced directly into a combustion chamber, and the combustion product is then directed to a mass spectrometer in a continuous, uninterrupted, automated process. Several problems have heretofore been encountered in the direct interfacing of a gas chromatograph and mass spectrometer through a combustion interface, which problems have degraded the precision heretofore obtainable by prior art on-line apparatus and methods.

In order to maximize precision of ion-current-ratio measurement in a mass spectrometer it is necessary that the vacuum in the mass spectrometer ion source and analyzer not be degraded. Degradation of mass spectrometer vacuum reduces ion source efficiency by causing a build-up of space charge in the ionization chamber, degrading focussing and extraction of the ion beam. Further deterioration of instrument performance results from interactions between neutral molecules and ions which cause increased scattering of the ion beam in the analyzer.

Large and varying flowrates exiting from conventional gas chromatographs, however, result in excessive pressures and pressure variations at the ion source of the mass spectrometer in on-line systems. Prior art apparatus and methods have attempted to reduce ion source pressure and pressure variations by splitting the effluent from the gas chromatograph. Apparatus such as jet separators or open splits have been employed to divert carrier gas away from the mass spectrometer. With such apparatus, however, a portion of the combusted sample is also diverted from the mass spectrometer. Precision is thus degraded in two ways: (i) less material is transmitted for ionization, resulting in weaker ion beams that are more difficult to measure, and (ii) because a portion of it is removed along with the carrier gas, $CO_2$ derived from the sample is liable to isotopic fractionation as it passes through the separator or splitter. There is, therefore, no assurance that the isotopic composition of $CO_2$ directed to the mass spectrometer is unaltered by the diversion of $CO_2$ by the jet separator or open split apparatus.

A palladium membrane has been used to selectively remove a hydrogen gas carrier to enrich the effluent introduced into a mass spectrometer in gas chromatography mass spectrometry (GC-MS) systems used for conventional organic analyses. Simmonds, P.G., Shoemake, G.R., Lovelock, J.E. (1970), "Palladium-Hydrogen System", *Anal-Chem* 42, 881–885; Lovelock, J.E., Simmonds, P.G., Shoemake, G.R. (1970). "The Palladium Generator-Separator-A Combined Electrolytic Source and Sink for Hydrogen in Closed Circuit Gas Chromatography", *Anal. Chem.* 42, 969–973; Dencker, W.D., Rushneck, D.R., Shoemake, G.R. (1972), "Electrochemical Cell as a Gas Chromatograph-Mass Spectrometer Interface", *Anal. Chem.* 44, 1753–1758. Specifically, the hydrogen carrier gas was removed by selective permeation through a palladium membrane, without any decrease in the amount of sample delivered to the mass spectrometer. Electrochemical palladium separators were used, for example, in the Viking lander spacecraft for organic GC-MS analyses on the surface of Mars The palladium separator thus makes possible the removal of a carrier gas, without loss of sample. Palladium membrane devices were largely abandoned as separators in the prior art, however, because they tended to degrade or hydrogenate samples, it was difficult to control their temperatures (the exothermic combustion of the separated hydrogen adjacent the membrane can produce a great deal of heat), and they were difficult and expensive to fabricate.

Palladium separators have not heretofore been used in connection with isotope-ratio-monitoring apparatus. In addition to the above-noted disadvantages encountered in structural GC-MS applications, prior art palladium separators were unable to accommodate the flowrates typically required in early isotope-ratio-monitoring gas chromatography - mass spectrometry (irm-GCMS) systems.

Thus, prior to the present invention, prior art attempts at automated isotope ratio monitoring have failed to provide the required quantitative precision, except with the use of time consuming, labor intensive off-line apparatus and methods requiring large amounts of sample.

SUMMARY OF THE INVENTION

The present invention is directed to an apparatus and method for performing precise on-line isotopic ratio monitoring. More specifically, the present invention is directed to an apparatus and method for determining the relative abundances of isotopes in organic compounds (such as the ratio of $^{13}C$ to $^{12}C$ isotopes). As discussed above, the isotopic ratio of a compound provides a wealth of information about the source of generation or formation of organic compounds.

Unlike the above-discussed prior art off-line systems, in which samples are purified into discrete components in a gas chromatograph, and the discrete components are collected in batches and then introduced in a separate procedure to a mass spectrometer for isotopic analysis, the present invention introduces combustion products of discrete sample components to a mass spectrometer directly as they exit from an interface connected to a gas chromatograph. The system thus operates in a continuous, uninterrupted, automated manner (i.e., on-line).

The interface of the present invention functions to overcome disadvantages encountered in the above-discussed prior art on-line systems which connect a gas chromatograph directly to a mass spectrometer for isotope ratio monitoring. In particular, the interface of the present invention is designed to buffer the mass spectrometer from excessive flowrates and variations in the flowrate exiting the gas chromatograph. Absent such buffering, the precision obtainable by the mass spectrometer is substantially degraded. Furthermore, with the present invention, the buffering of the mass spectrometer is achieved without removing any of the discrete components of the sample to be analyzed from the system. This is in contrast to prior art systems in which at least a portion of the discrete components of the sample to be analyzed is removed by the interface connecting the gas chromatograph to the mass spectrometer. The removal of a portion of the discrete components of the sample in such prior art systems introduces a lack of precision since less material is transmitted for ionization resulting in a weaker signal and the isotope ratio can be changed by the removal (i.e., the isotopes are fractionated).

The system is designed to have a small volume so that the discrete components of the sample exiting the gas chromatograph in a sequence do not commingle as they move through the interface to the mass spectrometer (i.e., so that there is no broadening of the bands of discrete components exiting the gas chromatograph).

The irm-GCMS system of the present invention, includes, in series, a gas chromatograph (GC) having a flame ionization detector (FID). a palladium separator, a combustion reactor having an oxygen source, a water separator and an isotope-ratio-monitoring dual inlet, dual (or triple) collector mass spectrometer (MS).

In accordance with the present invention, a sample to be isotopically analysed is introduced via a hydrogen carrier into the GC for resolution into its constituent compounds. As the sample is eluted from the chromatographic column of the GC, a small amount is diverted to the FID to monitor the progress of the process, and the remainder is directed to a palladium separator.

The palladium separator includes a palladium or palladium alloy membrane which selectively removes the hydrogen carrier gas via permeation. Simultaneously, a smaller volume of helium is mixed with the sample as a replacement carrier gas to move the eluted sample through the apparatus for further processing. Because the hydrogen is replaced by a small, scavenging flow of helium, a far more favorable gas load is ultimately introduced into the MS. Moreover, because the scavenging flow of helium is maintained absolutely constant, the gas load imposed on the mass spectrometer is rendered substantially insensitive to flow variations within the GC resulting from the GC temperature program variations, and the GC can be operated at its optimal flowrate without affecting MS performance.

From the palladium separator the sample and its helium carrier are delivered to a micro-volume combustion reactor, wherein the isotopic sample is oxidized to form carbon dioxide with carbon isotopic species (i.e., $^{12}CO_2$ and $^{13}CO_2$) in a ratio corresponding to the carbon isotopic ratio of the eluted compound. The combustion reactor includes a metal-oxide oxygen source. The metal-oxide oxygen source acts as a catalyst and permits quantitative combustion without introducing excessive oxygen gas to the system, which would degrade the performance and stability of the MS.

The scavenging flow of helium and combustion products from the combustion reactor are thereafter introducted into a water separator, which preferably includes a hygroscopic ion exchange membrane, such as Nafion tubing ("Nafion" is a du Pont trademark for a sulfonated, perflourinated, cross-linked polypropylene marketed principally for ion exchange applications). In the water separator, the water produced in the combustion reaction diffuses through the membrane and is swept away by a dry, inert purge gas to avoid performance degradation associated with the introduction of water into the MS.

From the water separator, the dry carrier gas and $CO_2$ are introduced into the MS, which is preferably a dual (or triple) collector isotope-ratio-monitoring MS. Minor modifications are made to the MS to accomodate gas throughputs in excess of those normally encountered in isotopic mass spectrometry and to avoid sample contamination and band broadening of the chromatographic peaks.

Means are provided for introduction of a standard of $CO_2$ for which the isotopic ratio is known, so that data from the irm-GCMS can be compared to a known standard in a manner conventional within the art.

Means are also provided to divert solvent peaks from the combustion interface. Such solvent peaks, if introduced into the interface, could deplete the available oxygen in the oxygen source and contaminate the MS ion source.

As will be appreciated from the foregoing, with the apparatus and method of the present invention, substantially all of the carbon from the organic sample is directed from the GC to the MS through the interface, thus avoiding precision losses associated with sample fractionation. Moreover, such sample is delivered at a flowrate and pressure suitable for high precision MS performance. Furthermore, because the system operates on-line (i.e., flow is continuous and uninterrupted), human intervention, analysis time and the required sample amount are substantially reduced from conventional off-line systems providing comparable performance.

Because total system volume is minimized and valves and similar hardware are not interposed in the effluent path, peak broadening is minimized and chromatographic resolution is retained throughout the system.

It is therefore an object of the present invention to provide an apparatus and method for determining isotopic ratios of samples with high precision in a continuous process with a minimal amount of time and human intervention.

It is a further object of the invention to interface a gas chromatograph with an isotope-ratio-monitoring mass spectrometer without degrading mass spectrometer performance.

It is still another object of the invention to provide an apparatus and method wherein a gas chromatrograph and mass spectrometer are connected on-line, and acceptable pressures are maintained in the mass spectrometer without degrading, altering or fractionating the isotopic composition of the sample being analyzed.

It is still another object of the invention to preserve chromatographic resolution of the effluent upon introduction in the mass spectrometer by minimizing the dead volume of the system and avoiding the placement of valves in the organic sample path.

It is still another object of the invention to provide an apparatus and method for diverting solvent peaks in an on-line isotope-ratio-monitoring gas chromatography-mass spectrometry system without substantially disrupting the flowrate to the MS.

It is yet another object of the invention to provide a method and apparatus for quantitatively combusting the effluent from a gas chromatographer while minimizing band broadening and the introduction of excessive flowrates of oxygen.

It is still another object of the invention to obviate the need for radioactive isotope tracer studies, thus reducing the risk of exposure to radioactivity to both subjects of experiments and labworkers.

These and other objects of the present invention will be apparent from the following description and the accompanying drawings of the preferred embodiment of the present invention.

DETAILED DESCRIPTION OF THE INVENTION

Figure 1:
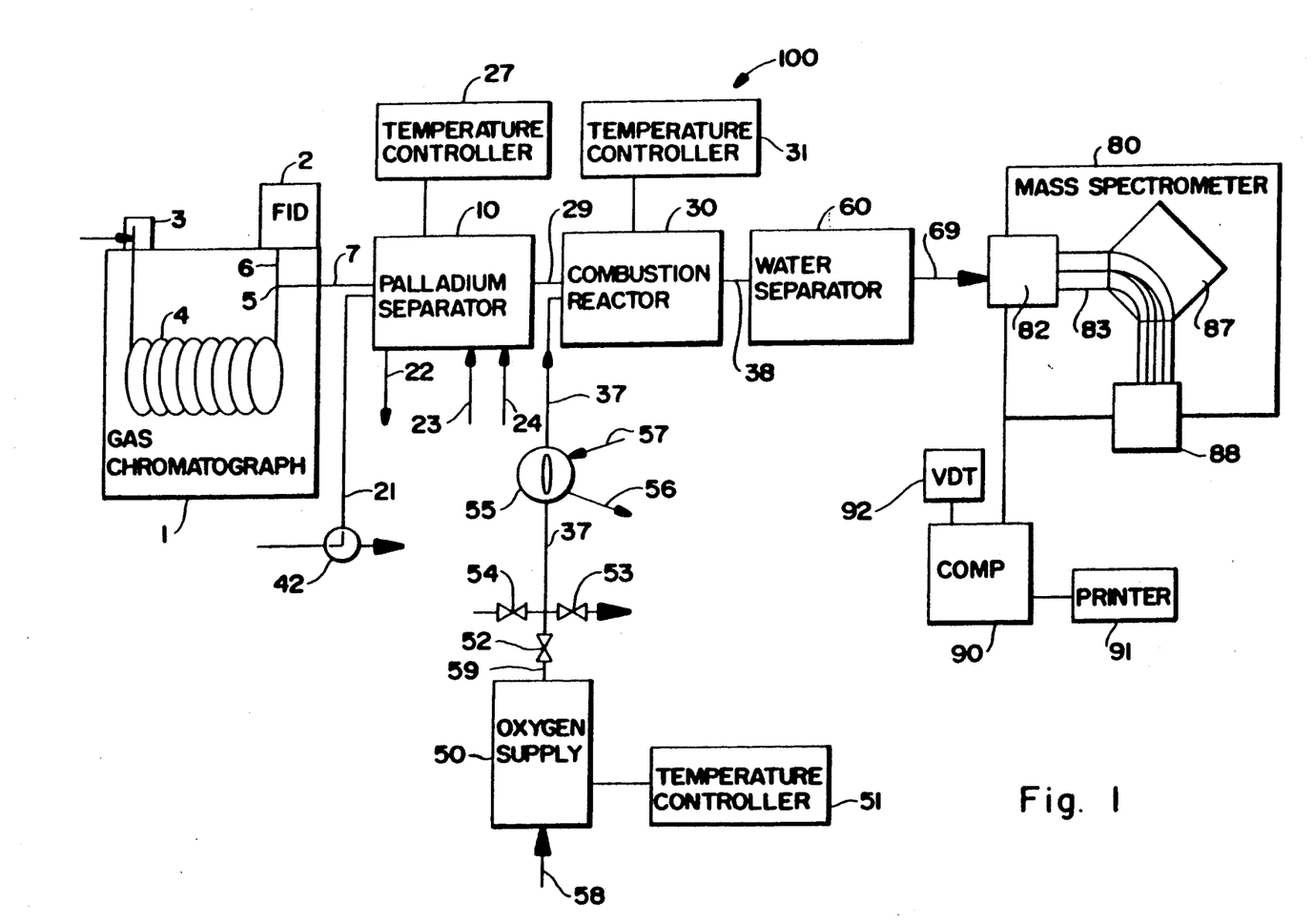
FIG. 1 is a schematic diagram of an apparatus and method in accordance with the present invention.

FIG. 1 schematically illustrates the irm-GCMS apparatus 100 of the present invention, with which the method of the present invention is performed. Specifically, the apparatus includes GC 1, palladium separator 10, combustion reactor 30, water separator 60 and isotope-ratio-monitoring MS 80 connected to computer 90.

Gas chromatograph 1 is conventional, and incorporates an FID 2, splitless injector 3 and a capillary column 4. Column 4 may be of any type, but an open tube capillary with bonded stationary phase will commonly be employed in order to improve resolution, reduce column bleed and reduce analysis time. Low bleed decreases the background signal in the MS. Improved resolution increases the distance between chromatographic peaks for the respective eluted compounds of the substance being isotopically analysed, thereby reducing the possibility of peak overlap. A suitable GC for use with the present invention is a Hewlett-Packard (Palo Alto, Calif.), Model 5890A.

Hydrogen is utilized as the carrier gas in GC 1. The effluent from GC 1 is divided via passive split 5 between FID 2 and the interface, which includes palladium separator 10, combustion reactor 30, water separator 60 and the components associated therewith. Split 5 divides the flow in column 4 between an FID capillary 6 and an interface capillary 7, which capillaries are dimensioned such that only a minimal amount of effluent is diverted to FID 2. A flow ratio of 1:25 between FID capillary 6 and interface capillary 7 has been used and produces overall acceptable system performance. As will be appreciated by those skilled in the art, other ratios could be implemented provided that the amount of diverted flow does not result in a substantial reduction in the amount of sample directed to the MS for analysis, impairing system sensitivity. FID 2 is useful to monitor system performance, but is not required, and can be eliminated if greater sensitivity is desired and the diversion of sample is sought to be avoided.

FID 2 combusts the effluent diverted through capillary 6 and includes suitable sensors for monitoring the ionization resulting from such combustion. The chromatographic effluent is continuously monitored by FID 2 and the output therefrom is communicated to computer 90. As discussed in more detail below, the primary function of FID 2 is to enable the operator to ascertain when solvent peaks are being eluted from GC 1, so that an appropriate solvent peak diversion routine can be performed.

Computer 90 is also connected to a controller of GC 1 to control the temperature program, such that a desirable resolution of chromatographic peaks is obtained.

As will be appreciated by those skilled in the art, the primary function of GC 1 is the resolution of a sample composition into discrete pure compounds for further analysis. GC 1 could thus be substituted with systems of sample resolution, including liquid chromatographic apparatus in which the eluted components were subjected to pyrolysis in a hydrogen stream after removal of the mobile phase. If resolution of mixed components is not desired, GC 1 could be substituted with an elemental analysis apparatus. Moreover, GC 1 could be eliminated in its entirety if pure gaseous compounds are to be analysed. Any other suitable means of resolving sample compositions into discrete, pure compounds could also be utilized.

Figure 2:
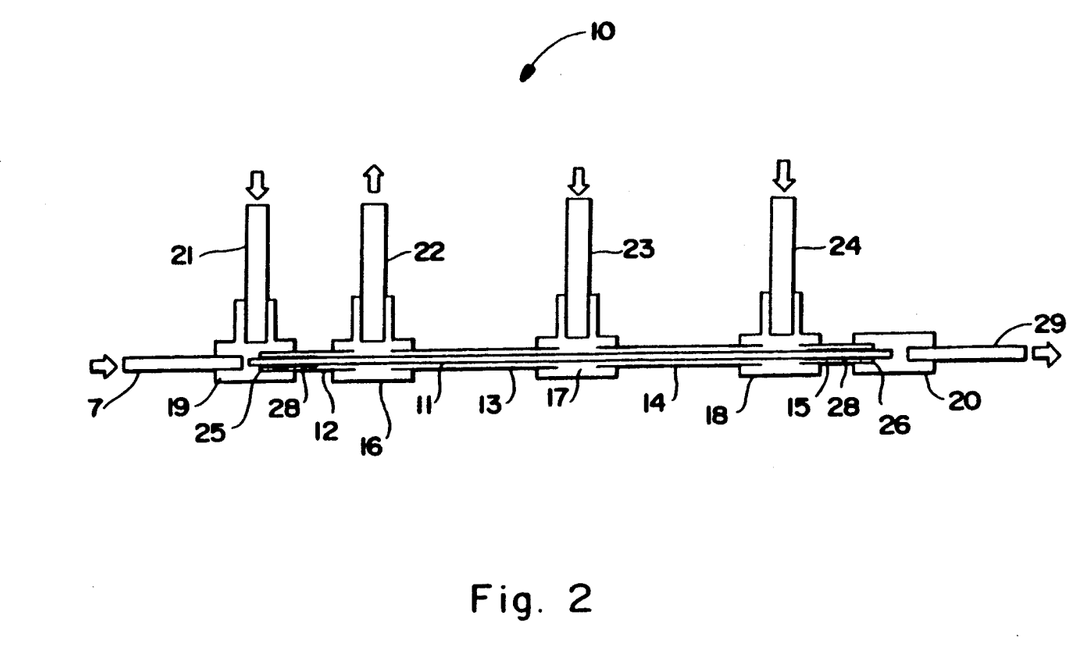
FIG. 2 is a schematic diagram of a palladium separator for use with the present invention.

The primary effluent flow from GC 1 is directed via capillary 7 to the first component in the interface, i.e., palladium separator 10. Palladium separator 10 functions to enrich the chromatographic effluent by removing the hydrogen gas carrier, and substituting a precisely constant scavenging flow of an inert carrier, preferably helium or any other conventionally utilized inert carrier gas. Operation of the palladium separator, shown in schematic detail in FIG. 2, is based upon the property of palladium and certain of its alloys that allows hydrogen, but not other gases or organic compounds, to readily diffuse therethrough.

Palladium separator 10 includes capillary or tube 11 made from palladium, or a palladium alloy to increase strength and reduce brittleness (e.g., an alloy of 81% should be sufficiently narrow to reduce dead volume, so that peak broadening does not result. The tube should, however, be long enough to ensure that complete hydrogen removal results. Palladium tube 11 is housed within a series of outer tubes 12–15, which can be made from stainless steel or any other suitable anti-corrosive material. Outer tubes 12 and 13 are joined in-line at adjacent ends by tee-connector 16. Adjacent ends of outer tubes 13 and 14, and 14 and 15, are similarly joined by tee-connectors 17 and 18, respectively. A fourth in-line tee-connector 19 joins capillary 7 from GC 1 to an adjacent end of outer tube 12. In-line connector 20 joins outer tube 15 with conduit 29 leading to combustion reactor 30. Conduit 29 may be made from platinum-iridium or any other suitable material.

At each end of the separator, short sleeves 28 made, e.g., from 95% gold and 5% platinum, concentrically center palladium tube 11 within outer tubes 12 and 15, respectively. The gold-platinum alloy sleeves are heated during assembly to form a flux-free solder joint 25 between the palladium tube and the outer tubes.

Conduits connected to tee-connections 17 and 18 are used to introduce purge gases into a chamber defined by the outer tubes and connectors and the palladium tube. Specifically, as discussed in more detail below, helium is introduced to tee-connector 17 via conduit 23, and air is introduced to tee-connector 18 via conduit 24. Conduit 22 from tee-connector 16 serves to exhaust water and the purge gases, as discussed below. Tee-connector 19 has conduit 21 through which a scavenging inert carrier gas, such as helium, is introduced to mix with the GC effluent carried within palladium tube 11, as discussed below.

The apparatus illustrated in FIG. 2 is contained within a suitable heating unit, such as an aluminum heating block heated by cartridge heaters (not shown). An iron-constantan thermocouple or other suitable temperature sensor monitors the temperature of the heating unit, and is connected to a temperature controller 27, which may be a Love (Wheeling, Ill.) Model 49 temperature controller or any other suitable apparatus. The heating unit is wrapped with suitable insulation material, such as magnesia-based insulation. The entire palladium separator unit 10 (including the manifold of tubes and conduits, the heating unit and the insulating material) is housed in an aluminum or other suitable case, which can be mounted on the external wall of GC 1.

In operation, the separator is maintained at an operating temperature ranging from approximately 250° C. to 300° C. The palladium tube 11 allows selective permeation of the hydrogen gas introduced at capillary 7 to the purge chamber defined by inner tube 11 and outer tubes 12–15 and tee-connectors 16–18. The helium and air purge gases introduced at conduits 23 and 24 purge the exterior of the tube 11 of hydrogen. As the air sweeps the exterior of the tube 11, the oxygen therein reacts with the diffused hydrogen to form water. The water is swept away by the stream of helium and remaining air. The helium further functions to cool tube 11, which would otherwise be thermally stressed by the heat produced by the exothermic oxidation of the hydrogen.

Removal of hydrogen from the exterior of the palladium tube reduces its partial pressure to near zero on the external tube surface, causing further diffusion of the hydrogen within the tube until all of the hydrogen is effectively removed from the interior of tube 11. Air inlet 24 is located at the downstream end of the separator, where the hydrogen partial pressure of the effluent is at its minimum. Because the hydrogen partial pressure of the air is also at its minimum when introduced, maximum separator efficiency is achieved where it is most needed, i.e., where the hydrogen content of the effluent is at its lowest.

A small and steady flow of helium (e.g., 250 microliters/min.) is added upstream of the separator at conduit 21 of tee-connector 19. The helium stream replaces the hydrogen as the carrier gas for the remainder of the process. The flowrate of this scavenging stream should be as low as possible to enhance MS performance, but must be sufficiently large to carry the compound through the system for further processing (e.g., combustion, water removal, etc.). As is apparent from the foregoing, the flowrate of the replacement stream of helium is independent of the GC effluent flowrate, and does not vary with the temperature program of the GC. Accordingly, the substitution of the carrier gas via palladium separator 10 enables both the GC and MS to be operated at their optimal flowrates without compromise. Moreover, because the entire sample is delivered, and only the hydrogen carrier is removed, isotopic fractionation of the sample does not result.

Many of the difficulties encountered with prior art uses of palladium separators for carrier gas removal are not encountered by the present invention. Specifically, the construction of the present invention overcomes heating difficulties, as the purge gases are used both to cool and carry away the permeated hydrogen (in the form of water). Moreover, it is unimportant if the sample is degraded or hydrogenated in the present invention, so long as carbon is not lost or exhausted, since the sample is ultimately burned in combustion reactor 30. Also, improvements in system sensitivity resulting from, e.g., reductions in system dead volumes, improvements in system flow characteristics and improved isotope-ratio-monitoring MS equipment render possible flowrates at which a palladium separator can be advantageously employed. Furthermore, improvements in the palladium separator, including the provision of a replacement flow of helium, make the interfacing of a GC and an MS possible in isotope-ratio-monitoring systems by improving flow characteristics to the MS, while still ensuring that the sample is carried through the system without unacceptable band broadening.

From the palladium separator 10, the organic compound and helium carrier gas are directed via conduit 29 to combustion reactor 30. Conduit 29 is made from a suitable material, such as platinum-iridium. The combustion reactor, illustrated schematically in greater detail in FIGS. 3 and 4, functions to convert the organic compound to carbon dioxide having abundances of $^{12}CO_2$ and $^{13}CO_2$ in a ratio corresponding to the isotopic ratio of the compound.

Figure 3:
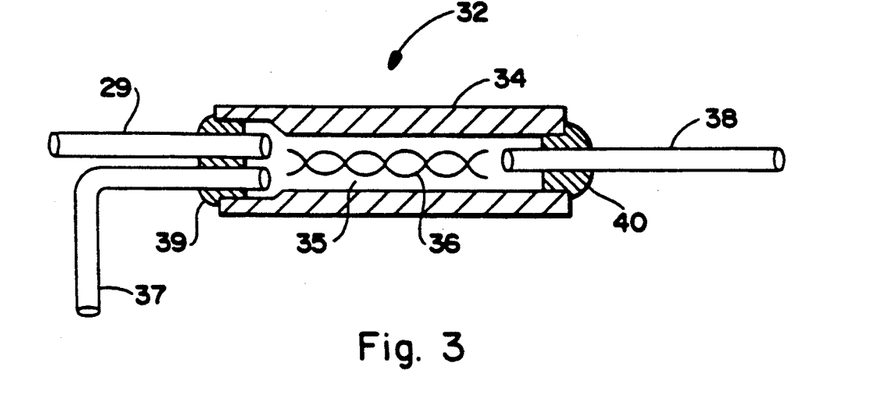
FIG. 3 is a schematic diagram of a combustion reactor reaction column for use with the present invention.
Figure 4:
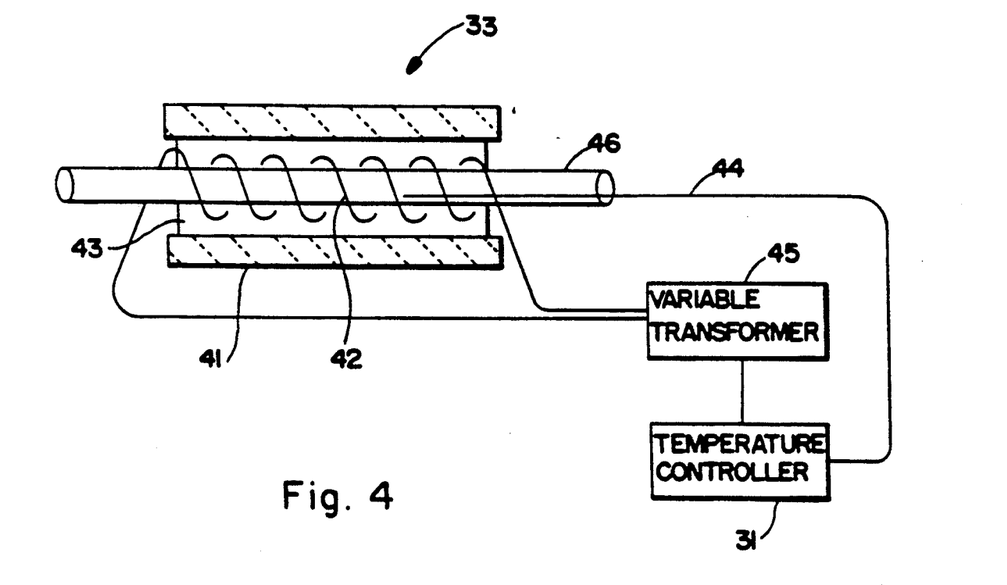
FIG. 4 is a schematic diagram of a combustion reactor furnace for housing the combustion reactor column of FIG. 3.

The combustion reactor 30 consists of two basic components: a reaction column 32 and a resistively heated furnace 33.

Reaction column 32 includes thick-walled quartz capillary or tubing 34 defining a micro-volume combustion chamber 35. Chamber 35 is packed with combustion catalysts and an oxygen donor, such as platinum and oxidized copper wire 36, respectively. The platinum catalyst promotes the combustion reaction of organic carbon. When copper wire 36 is oxidized within the chamber, an outer layer of cupric oxide (CuO) forms thereon. The copper wire is initially oxidized at 600° C. under a flow of oxygen. Although CuO is the preferred metal-oxide for use in chamber 35, other oxidized compounds could be used, including cobalt oxide $Co_3O_4$ or the decomposition product of silver permanganate. Additionally, although the metal-oxide is disclosed herein in wire form, granular or mesh forms in suitable volume providing the requisite surface area could also be utilized.

Conduits of suitable material, e.g., platinum-iridium, are located at the ends of the quartz tubing 34. Specifically, conduit 29 from the palladium separator and conduit 37 from oxygen supply 50 (discussed below) are located at the upstream end of quartz tubing 34 and conduit 38 leading to a water separator 60 is located at the downstream end of quartz tubing 34.

Seals 39, 40 are formed at each end of column 32 between the conduits 29, 37, 38 and the quartz tubing 34. The seals are made from suitable material, such as silver chloride melted by heat conducted through quartz tubing 34. When melted, the silver chloride is drawn by capillary action between the quartz tubing 34 and conduits 29, 37, 38. After cooling, the silver chloride forms a durable leak-tight seal.

FIG. 4 illustrates resistively heated furnace 33, which houses a quartz sleeve 46. Reaction column 32 (FIG. 3) is mounted within quartz sleeve 46.

Quartz sleeve 46 is wrapped with high resistance wire 42, such as chromel-alumel wire (28 gauge), which is thereafter coated with a heat resistant corrundum and mullite based cement (alundum) 43, or other suitable thermal and electrical insulating material. A ceramic tube 41 protects the friable alundum coating 43.

Quartz sleeve 46 is dimensioned such that its ends and the ends of reaction column 32 housed therein extend beyond ceramic casing 41 of furnace 33, so that the silver chloride seals (melting point 450° C.) in the reaction column do not melt during operation of the furnace.

The temperature in chamber 35 is monitored by a suitable detector, e.g., a k-type thermocouple (chromel-alumel) positioned between quartz sleeve 46 and quartz tubing 34. Temperature is controlled by a temperature controller 31, which can be similar to temperature controller 31, and a variable transformer 45.

The temperature of conduit 29 is maintained substantially at the temperature of the palladium separator (e.g., 300° C.) by encasing the conduit in insulation, and is monitored via a suitable temperature sensor.

In the preferred embodiment, the combustion reactor is heated to a temperature of approximately 800° C., and the effluent (comprised of the organic sample and the helium carrier) output from palladium separator 10 via conduit 29 is introduced into combustion chamber 35. Combustion chamber 35 should have as small a volume as is practicable to ensure that the effluent moves readily therethrough to avoid band broadening (which reduces spacing between the chromatographic peaks). The metal and metal-oxide within chamber 35 function as both a catalyst and an oxygen source for oxidation of the organic sample entering the chamber. Accordingly, the organic molecules are combusted, utilizing the partial pressure of oxygen in an equilibrium state above the metal-oxide, to form carbon dioxide and water (and other combustion products if other elements are present, e.g., $N \rightarrow N_2$, $S \rightarrow SO_2$), which are exhausted with the carrier gas through outlet conduit 38 to water separator 60.

Although the oxygen in equilibrium above the metal-oxide 36 should be sufficient to oxidize all of the organic material in a normal run (provided the solvent diversion procedures discussed below are followed), an additional oxygen supply 50 is provided. Oxygen supply 50 provides additional oxygen for use during chromatographic peaks and regenerates (or reoxidizes) the deoxidized metal in chamber 35 during non-peak periods.

The introduction of large flows of oxygen into the system will damage or degrade the ion source of MS 80 and, as portions of the oxygen flow are periodically consumed by processes of combustion, upset the stability of flow delivered to the MS. It is thus desirable that oxygen be introduced into the system only at extremely low partial pressures. To this end, oxygen supply 50 is provided to introduce low (trickle) levels of oxygen in a helium carrier to combustion reactor 30 via tube 37.

Oxygen supply 50 can be constructed similar to reaction column 32, except that it has only a single inlet conduit 58 at its upstream end and is much larger. Oxygen supply 50 includes a quartz tube filled with a suitable amount of CuO (e.g., 500 grams) or other metal-oxide, and is heated by a resistive mechanism controlled by temperature controller 51. The oxygen supply is preferably heated to a temperature slightly above the temperature of the combustion reactor (e.g., 850° C.) to ensure that the equilibrium oxygen pressure of oxygen source 50 is slightly (e.g., 10%) above the equilibrium dissociation pressure of oxygen within combustion chamber 35. A low flowrate of helium carrier gas is introduced at the upstream end of the oxygen supply via conduit 58, and passes through the oxygen supply, carrying with it the molecular oxygen suspended above the metal-oxide at its equilibrium partial pressure. The helium and molecular oxygen are thereafter exhausted through conduit 59. The level of oxygen supplied is variable, and is a function of the temperature at which temperature controller 51 is set. Specifically, an increase in temperature results in an increase in the equilibrium partial pressure of oxygen, and a similar increase in the amount of oxygen supplied by oxygen supply 50 to the combustion reactor.

The helium and oxygen exiting from conduit 59 thereafter flow through on-off valve 52 to conduit 37. Conduit 37 is selectively vented to the atmosphere via on-off valve 53 and is selectively connected directly to a helium source via on-off valve 54. Valves 52, 53, 54 are operated in connection with the solvent peak diversion process described in detail below. During normal flow: valve 52 is open, valve 53 is open and vented to the atmosphere and valve 54 is closed.

A four-port sampling valve 55 is interposed between oxygen supply 50 and combustion reactor 30. Sampling valve 55 is provided to selectively introduce aliquots of a known standard or sample, as described in more detail below. During normal operation, sampling valve 55 is set such that flow passes directly through conduit 37 from oxygen supply 50 to combustion reactor 30. In these circumstances, the helium/oxygen mixture delivered through conduit 59 will be transmitted to the combustion furnace through conduit 37 whenever the withdrawal of gas from the combustion furnace (through conduit 38) causes the pressure at the inlet of conduit 37 to drop below one atmosphere.

As described in more detail below, MS 80 includes pumps for creating a low pressure (e.g. $3.5 \times 10^{-6}$ mbar) in the MS ion source. The flowrate through the system is determined by the system configuration and the pressure drop across the system. A fixed flowrate of helium is introduced, as noted above, at conduit 21 of palladium separator 10. Accordingly, the additional required flow for the defined system pressure drop and system configuration is provided by the drawing in of helium and oxygen through conduit 37 during normal operation.

Although the above oxygen supply advantageously provides low levels of oxygen to the system via passive fluid flow, it will be appreciated that other appropriate oxygen supply means could be utilized in lieu of the above-described oxygen supply apparatus. Specifically, any oxygen supply which provides a low flow of oxygen of adequate purity could be used for this purpose.

Numerous advantages are achieved by the combustion system of the present invention. Specifically, the incorporation of a chemical oxygen donor within the combustion furnace satisfies the oxygen requirement for quantitative combustion of momentarily high loads of oxidizable material, without introducing oxygen flowrates which would sharply degrade MS performance. Moreover, the implementation of a supplemental oxygen supply comprised of a chemical oxygen donor or other constant, low pressure oxygen source greatly enhances the performance of the combustion system of the present invention. Specifically, in the absence of a supplemental oxygen supply, the in-furnace donor reservoir of oxygen would have to be increased to avoid the requirement for frequent recharging thereof. Such an increase in size, however, would require that the combustion chamber 35 be of such a size that chromatographic resolution would be substantially impaired (i.e., dead space losses would be incurred). Alternatively, if the chamber is made to dimensions resulting in acceptable resolution, but no supplemental flow like that in the present invention is employed, the overall oxidizing capacity of the furnace would be too low for most practical applications.

With the combustion system of the present invention, a near-zero volume combustion system is achieved without sacrificing combustive efficiency, system resolution or system maintenance considerations.

The passive compensation of helium/oxygen flow provided by the combustion system through conduit 58 provides still further significant performance advantages. Absent this feature of the invention, the pressure in combustion chamber 35 would be determined solely by the balance between its input and output flows. If the incoming helium flow were to exceed the gas flow withdrawn from the downstream end of the combustion chamber by the mass-spectrometer vacuum system (working through leak 81 and separator 60), the pressure inside the combustion chamber would rise, possibly rupturing the end seals on the combustion chamber and almost certainly causing maintenance problems. If, on the other hand, the downstream gas demand were to exceed the input through tube 29, the pressure in the combustion chamber would decrease, possibly causing atmospheric gases to leak in. Even if the combustion chamber were perfectly gas tight, the decreased pressure (possibly approaching a vacuum) would result in band broadening due to loss of laminar flow and in decreased residence time of sample molecules in the combustion system. Such decreased residence time would very likely lead to incomplete combustion and seriously erroneous results. The system including conduit 37 and its associated subsystems completely avoids these critical problems. Not only does it supply oxygen gas (as noted above), it also stabilizes the pressure in the combustion reactor, thereby stabilizing gas flows into the mass spectrometer and optimizing sample residence times in the combustion chamber.

Even if one skilled in the art were able to stabilize and control the combustion chamber inlet and outlet flows such that the pressure problems described above would not develop, pressure fluctuations associated with the process of combustion itself would still be encountered. During combustion, a single molecule, say a large hydrocarbon, creates many product molecules (carbon dioxide and water). In the present invention, even those pressure surges are buffered by connection to an absolutely constant pressure source (i.e., the atmosphere) through valve 53.

Water is an abundant product of the combustion reaction in combustion reactor 30. Such water must be removed before introducing the organic sample to MS 80 to prevent proton transfer reactions from occurring in the ion source. Specifically, the addition of a proton to $^{12}C^{16}O_2$ would cause its molecular mass to increase from 44 to 45, thus introducing systematic errors into the isotope ratio measurements (since 45 is also the molecular mass of $^{13}C^{16}O_2$).

Many prior art isotope GCMS systems employ cryogenic traps in order to remove water from the effluent. Such apparatus trap water, but do not entirely remove the water from the system. Consequently, the $CO_2$ and carrier gases are exposed to the surface of the condensed water, which can result in adsorption of the gases on the water ice. Such adsorption can result in peak broadening, thus decreasing the resolution of the chromatographic peaks.

Although apparatus of the above type could be employed, the present invention preferably employs apparatus as described below for removing water from the system entirely. Water separator 60, schematically illustrated in FIG. 5, utilizes a tubular hygroscopic ion exchange membrane 61 which allows water, but not $CO_2$, to permeate therethrough. A suitable material for tube 61 is Nafion. Water is removed through the Nafion tubing without exposing the effluent to condensed water or other adsorbents. Selectively permeable tube 61 should have minimal dead volume to ensure laminar flow of the effluent and to avoid peak broadening which degrades resolution, and sufficient length to ensure that all water is removed.

Figure 5:
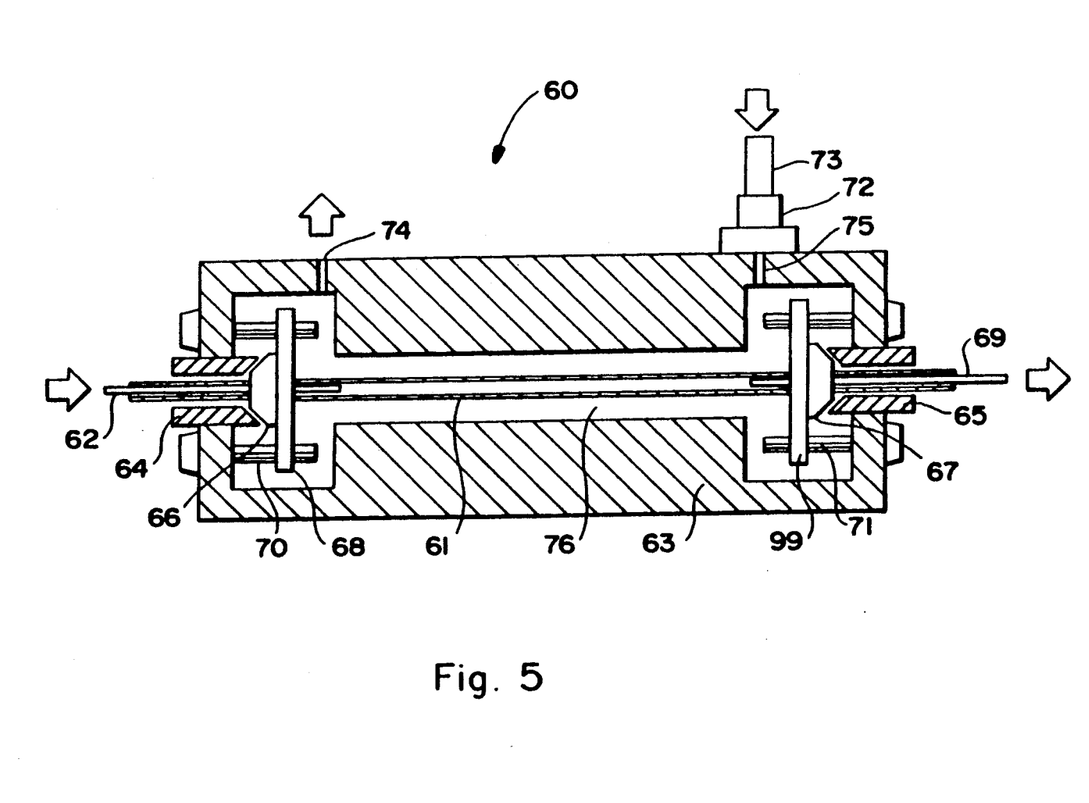
FIG. 5 is a schematic diagram of a water separator for use with the present invention.

Two short lengths of vitreous silica capillary 62, 69 are inserted at the respective ends of tube 61. Capillary 62 is connected via a zero dead-volume connector to platinum-iridium output conduit 38 from combustion reactor 30. Capillary 69 is connected via a zero dead-volume connector to the downstream end of a vitreous silica capillary leak 81 leading to the ion source of MS 80. Alternatively, capillary 69 can be extended directly to the ion source of MS 80 and capillary 81 can be eliminated.

Tube 61 is housed in a casing or block 63 of aluminum or other suitable material. Because tube 61 is fragile and will readily wear or fracture if subjected to torque, support structure is provided to firmly secure tube 61 within casing 63, while isolating it from torque. Casing 63 has unions 64, 65 at its respective ends which cooperate with respectively graphite ferrules 66, 67, metal plates 68, 99 and hex-head screws 70, 71 to support tube 61 within the housing. Tube 61 is supported by openings in graphite ferrules 66, 67 and metal plates 68, 99. Metal plates 68, 99 have threaded openings adapted to receive hex-head screws 70, 71. The tightening of hex-head screws 70, 71 respectively draws metal plates 68, 99 towards the respective ends of casing 63, thereby urging graphite ferrules 66, 67 into sealing engagement with unions 64, 65. Metal plates 68, 99 isolate tube 61 from torque as screws 70, 71 are tightened.

Connector 72 is mounted on a side of casing 63, and connects a conduit 75 in the casing to a conduit 73 connected to a dry, inert purge gas source. A suitable purge gas is argon, which has been dried via a magnesium percholate trap in a conventional manner. Conduit 75 communicates with purge chamber 76, in which tube 61 is mounted. A conduit 74 serves as an outlet for the purge gas and water carried thereby, as described below.

In operation, effluent, including helium, $CO_2$ and water, is input to water separator 60 from combustion reactor 30 via capillary 62. Because tube 61 is permeable only to water, water diffuses through tube 61 and is swept away by the dry, inert purge gas entering purge chamber 76 via conduit 75. The purge gas reduces the partial pressure of water on the exterior of tube 61, causing more water to diffuse therethrough. The purge gas and permeated water are thereafter exhausted via conduit 74. Dried effluent (helium and $CO_2$) is thereafter exhausted via conduit 69. As illustrated in FIG. 5, the purge gas is introduced in the reverse direction of the gas flow inside the tube 61. This reverse flow establishes a reverse water vapor gradient, such that the driest purge gas (having the lowest water vapor pressure) is at the end of the tube having the lowest internal vapor water pressure. The reverse water vapor gradient thus operates to improve the water removal efficiency of water separator 60.

Figure 6:
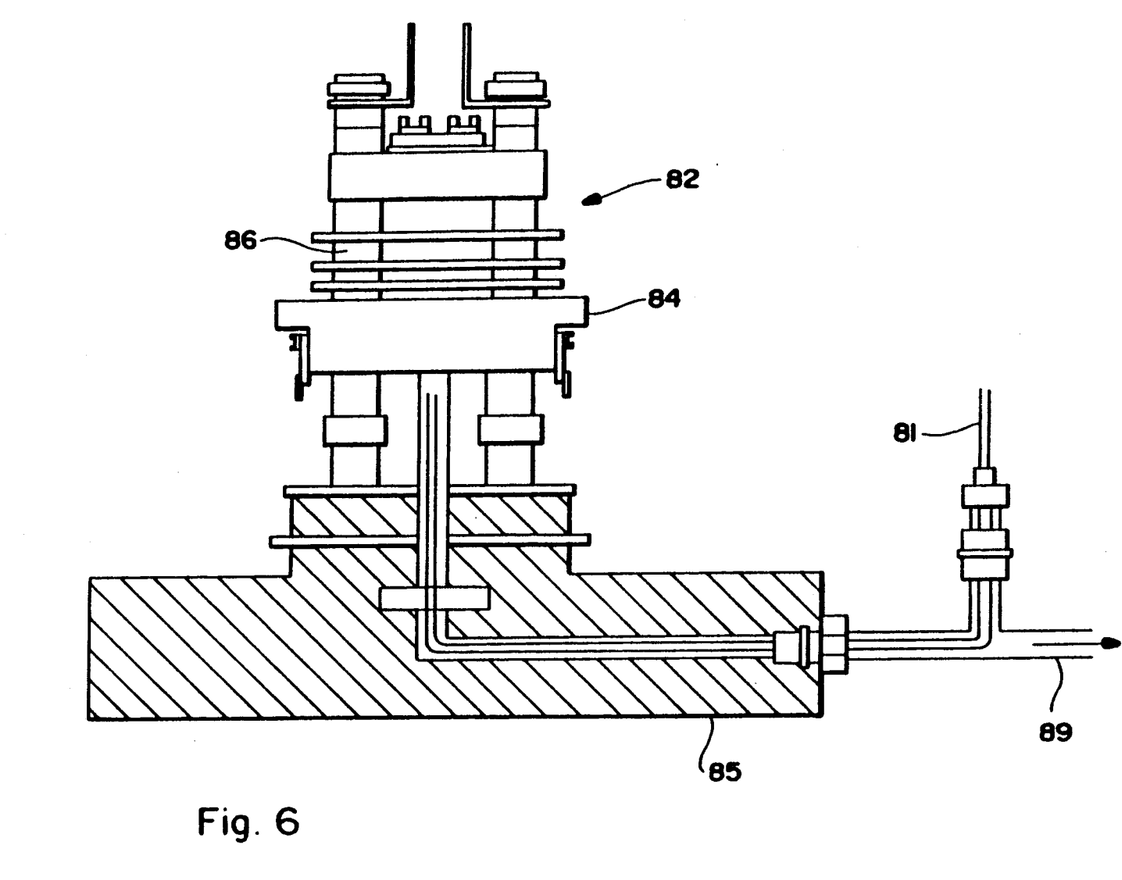
FIG. 6 is a schematic diagram of an ion source of an isotope ratio monitoring mass spectrometer for use with the present invention.

From water separator 60, effluent is transferred to vitreous silica capillary 81 of MS 80. MS 80 is a conventional dual inlet, dual (or triple) collector isotope-ratio-monitoring mass spectrometer, which preferably incorporates differential pumping. Differential pumping (i.e., two pumps: one pump attached to the ion source housing 82 to consume the bulk of the gas and a second pump attached to the analyzer section 83 to maintain a lower pressure over the length of the ion flight path) is desirable to accomodate the flowrates of effluent into the ion source, which may otherwise lead to pressures above those allowing for best performance of MS 80 because of the addition of helium to the effluent to carry the $CO_2$ through the on-line system. One suitable MS is the Finnigan MAT delta S(ystem). MS 80 ionizes $^{12}CO_2$ (molecular mass =44) and $^{13}CO_2$ (molecular mass =45) isotopes in ion source 82, accelerates the ions via accelerator 83 and deflects them via a magnetic source 87 to collecters 80 for isotope detection, in a conventional manner. A third collector may be used to detect molecular masses of 46, corresponding to $CO_2$ molecules containing $^{18}O$ isotopes. The $^{18}O$ values can thereafter be used to correct the collected data for oxygen isotopic contributions. MS 80 is connected to computer 90 having printer 91 and visual display terminal 92 for data analysis. From the detected abundances of carbon isotopes, an isotopic ratio for the sample eluted from GC 1 can be calculated.

The transfer capillary or leak 81 from the interface runs directly to the entrance of the ionization chamber 84 of ion source 82 through ion source flange 85. The extension of leak 81 directly to the ion source represents a modification of conventional MS ion sources, and is employed to prevent excess exposure and possible adsorption of the $CO_2$ molecules from the organic sample to the stainless steel walls of flange 85 and other ion source structure. Such adsorption would otherwise have the effect of peak broadening, thus impairing the chromatographic resolution.

The dimensions of capillary 81 are selected to control the desired flowrate in the system. Specifically, since the pressure drop across the system is defined (from atmospheric pressure (1 bar) at on-off valve 53 to approximately $3.5 \times 10^{-6}$ mbar in the ion source), as is the remainder of the system configuration, the length and diameter of capillary 81 can be selected to restrict the effluent flow to the MS to a desired amount, e.g., 500 microliters/min. If, for example, the scavenging flowrate of carrier gas introduced through conduit 21 is 250 microliters/min., selection of dimensions of capillary 81 such that 500 microliters/min. are withdrawn through conduit 69 will cause 250 microliters/min. of the helium/oxygen mixture to be drawn into the system through conduit 37.

It may also be desirable to modify MS 80 to ensure that pressure levels within the ionization chamber are maintained at suitable levels. To this end, the ion source can be opened to increase its conductance, and thereby reduce pressure therein. One method of opening the ion source is to remove all or part of the conventional ceramic rings (not shown) surrounding ion accelerator 86. As will be appreciated by those skilled in the art, other methods of opening the ion source or otherwise reducing pressure therein could be employed.

As briefly mentioned above, it is desirable in conventional isotopic analysis to compare the isotopic ratio calculated for an eluted sample to that of a standard of known isotopic composition. To this end, a known sample can be introduced during the time period between chromatographic peaks via conduit 57 at toggle valve 55.

Sampling valve 55 connects either conduit 57 or the upper portion of conduit 37 directly to combustion reactor 30 (whichever conduit is not selected is vented through conduit 56). As will be appreciated by those skilled in the art, the $CO_2$ standard need not be introduced at valve 55, but could instead be introduced at any convenient portion of the system, including inlet 3 of GC 1, the unused inlet 89 (FIG. 6) of MS 80, or by means of a switching valve installed in the downstream end of capillary 81. The standard can also be introduced through a dummy chromatographic column to simulate the peak formations of the sample to which it is to be compared. The isotopic ratios obtained from the standard can thereafter be used for measurements of system sensitivity, precision and accuracy.

In operation of the system, it is desirable that large solvent peaks eluted from GC 1 be diverted from entering the combustion interface. Such peaks would deplete the oxygen in the metal-oxide of combustion reactor at a rate greater than oxygen supply 50 could resupply such oxygen for the next sample peak. Moreover, to avoid fractionation of the eluted isotopic sample, it is desirable that such diversion be achieved without interposing valves or similar structure in the effluent path to avoid fractionation of the sample and band broadening of the chromatographic peaks.

Solvent peak diversion can be accomplished with the present invention via on-off valves 52, 53, 54 in conduit 37 and an additional valve 92 (FIG. 1) in conduit 21. Valve 92 is a two position valve which selectively connects conduit 21 to a helium source or vents conduit 21 to the atmosphere. In the solvent peak diversion mode, all solvent is directed away from the interface and exhausted through conduit 21.

The valves are configured as follows during the solvent peak diversion mode: valve 52 is closed to prevent flow from oxygen supply 50; valve 54 is opened to a pressure (greater than atmospheric) sufficient allow helium to flow in conduit 37 at a predetermined rate; valve 53 is closed, blocking the vent to the atmosphere; and valve 92 is positioned to vent conduit 21 to the atmosphere.

The introduction of pressurized helium at valve 54 causes helium to flow through conduit 57, and split at the combustion reactor. A portion of the flow is drawn towards MS 80 due to the pressure drop between conduit 57 and MS 80. The remaining portion of the flow is diverted through the palladium separator and vented at atmospheric pressure through valve 92 in conduit 21. Because conduit 21 is at atmospheric pressure and conduit 37 (and the palladium separator) are at greater than atmospheric pressure, the effluent from GC 1 (including the solvent) flows through conduit 21 and is vented to the atmosphere.

The apparatus is operated in the solvent peak diversion mode at the beginning of the run until the solvent peak is diverted (as noted from the output of FID 2). The system is thereafter returned to normal flow by reconfiguring valves 52, 53, 54 and 92, and the GC temperature program is started. As will be appreciated by those skilled in the art, solvent peak diversion and normal flow can, however, be implemented at any appropriate point in the operation of the apparatus. Furthermore, valves 52, 53, 54 and 92 could be controlled by the computer and automatically reconfigured from the sample diversion mode to the normal flow mode upon detection of the end of the solvent peak at FID 2.

Furthermore, although the preferred method of solvent peak diversion has been discussed, other methods could be implemented without departing from the scope of the invention. Such methods should preferably, but need not, avoid interposing valves or related structure in the effluent path.

Figure 7A:
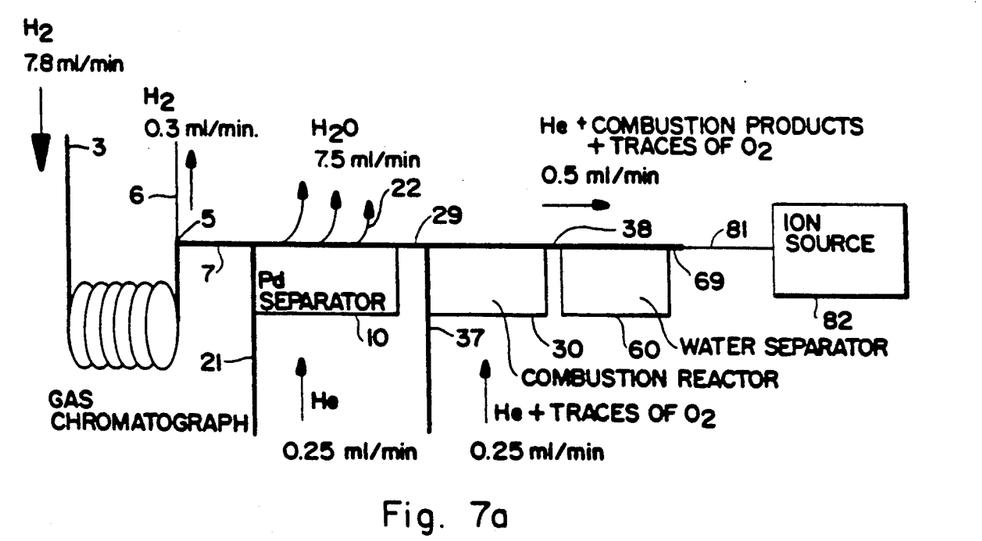
FIGS. 7a and 7b are schematic illustrations of exemplary flow conditions during normal operation and solvent peak diversion modes, respectively.
Figure 7B:
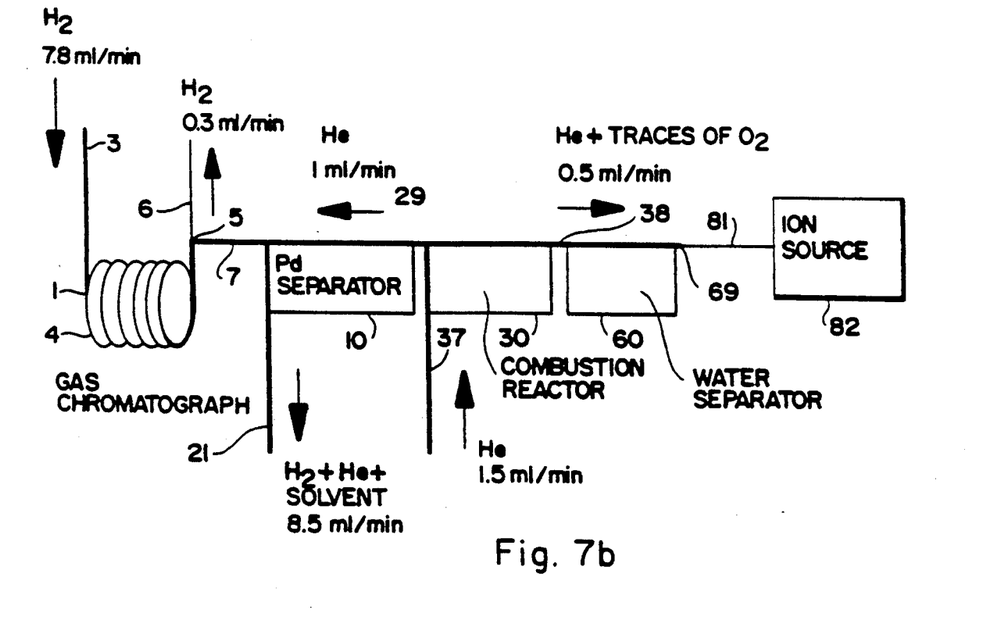

Having described the apparatus and method of the present invention, a description of an exemplary procedure follows, with reference to FIGS. 7a, 7b and previously discussed FIGS. 1–6. FIGS. 7a and 7b refer to flowrates which are included for exemplary purposes, and do not represent or limit actual flowrates for an actual run. Such flowrates, however, demonstrate the system dynamics and the order of magnitude and relative values of flowrates encountered in the preferred embodiment of the invention.

In the preferred embodiment, a solvent is selected which will be eluted from GC 1 prior to the compounds of the sample to be isotopically analyzed. Accordingly, valves 52, 53, 54 and 92 can be initially configured in the solvent peak diversion mode to direct the GC effluent away from the combustion interface.

FIG. 7b illustrates exemplary flowrates during the solvent peak diversion made for a sample inlet flowrate of 7.8 ml/min. (sample plus hydrogen carrier gas) at inlet 3 of GC 1. As illustrated in FIG. 7b, 1.5 ml/min. of helium is introduced at valve 54 to conduit 37 at a pressure exceeding atmospheric pressure. The helium flow from conduit 37 is split between MS 80 and palladium separator 10, by an amount determined by the system dynamics and pressures (e.g., 0.5 ml/min. to MS 80 and 1.0 ml/min. to palladium separator 10). A portion of the effluent from GC 1 (e.g., 0.3 ml/min.) is diverted to FID 2 via conduit 6. The remainder of the effluent (e.g., 7.5 ml/min.) is directed through conduit 7. Because conduit 21 is vented to the atmosphere and pressurized helium is introduced at valve 54, the remaining GC effluent exhausts along the path providing the greatest pressure drop, i.e., conduit 21, and is thus diverted from the interface as illustrated in FIG. 7b.

After the operator determines from monitoring the output of FID 2 at VDT 92 that all of the solvent has been diverted (i.e., that the solvent peak has been eluted), valves 52, 53, 54 and 92 are reconfigured to their normal operating positions and normal flow commences as illustrated in the exemplary flow diagram of FIG. 7a.

The operator then commences the temperature program in GC 1, in a conventional manner, to provide optimum peak resolution and band width. The exemplary flowrate at the inlet continues at 7.8 ml/min. (sample plus hydrogen carrier) as illustrated in FIG. 7a, of which 0.3 ml/min. is diverted to FID 2, and the remaining 7.5 ml/min. is directed to the combustion interface via conduit 7.

Carrier gas substitution is thereafter performed at 300° C. by palladium separator 10, such that 7.5 ml/min. of hydrogen (less the sample volume) is exhausted and substitute helium carrier gas is added at a suitable flowrate, e.g., 0.25 ml/min.

The reduced volume of effluent (helium and sample) is thereafter directed to combustion reactor 30 via conduit 29, wherein the organic sample is oxidized at 800° C. to form $CO_2$, water, and other products of combustion (for example, $N_2$ if nitrogen is present) suspended in a helium carrier. Additional helium and replenishing oxygen (e.g., 0.25 ml/min) are added to the effluent by oxygen supply 50 via conduit 37. The actual flowrate of helium and oxygen through conduit 37 is passively determined by the system configuration, including the dimensions of leak 81 to MS 80, and by the pressure drop between conduit 37 and MS 80 (i.e., from atmospheric pressure in conduit 37 to $3.5 \times 10^{-6}$ mbar in MS 80). The total effluent, including the helium carrier, water and $CO_2$ (including $^{12}CO_2$ and $^{13}CO_2$) are thereafter introduced to water separator 60.

Water separator 60 removes the water from the effluent and directs the remaining effluent, including all of the combusted carbon, directly to MS 80 for isotopic analysis.

Because isotope-ratio-monitoring MS 80 has dual (or triple) collectors, no precision losses associated with scanning are encountered. As will be appreciated, however, a single collector (e.g., magnetic sector or quadrupole) MS could be implemented if appropriate corrections are made and a lesser precision is required.

Additionally, although disclosed in connection with carbon isotope-ratio-monitoring, the invention need not be so limited, and could be used to measure other isotopic compounds, including nitrogen, with only minor modifications. Such modifications should include the inclusion of an on-line trap for removing $CO_2$ resulting from combustion in the combustion reactor.

Still further modifications to the invention can be made without departing from the spirit thereof, including changes in the composition of the carrier and purge gases used in the system. If, however, a carrier gas other than hydrogen is used in GC 1, a suitable material must be employed in separator 10 which ensures that only the carrier gas permeates and separates from the sample.

Furthermore, while the replacement or scavenger flow of helium has been described as being added in the palladium separator via conduit 21, it will be appreciated that the helium could be mixed with the hydrogen upstream of the palladium separator and even upstream of the gas chromatograph. In such an application, conduit 21 of palladium separator could be eliminated.

The scope of the present invention is not limited to the precise embodiments disclosed. Still further possible modifications, variations and changes to the present invention as described in the present specification and illustrated in the figures will be appreciated by those skilled in the art, without departing from the scope and spirit of the present invention.

What is claimed is:

1. A method for determining isotopic abundances of at least one substance in a mixture in a single continuous process, comprising the steps of:
   mixing the mixture with a first carrier gas;
   introducing the mixture and first carrier gas into a gas chromatograph to resolve the mixture into at least one discrete substance mixed with the first carrier gas;
   eluting said at least one discrete substance and first carrier gas from said gas chromatograph to an interface;
   separating in said interface all of said first carrier gas from said at least one discrete substance such that all of said discrete substance remains within said interface for further processing;
   combusting said discrete substance to form a combustion product mixture having a plurality of combustion products; and
   directing at least one of said combustion products to an isotopic mass spectrometer for determination of isotopic abundances;
   wherein said at least one discrete substance is eluted from said gas chromatograph in a discrete band having a measurable width, and the width of said band is not substantially increased as said at least one discrete substance moves through said interface to said mass spectrometer.

2. The method for determining isotopic abundances of at least one substance in a mixture in a single continuous process as set forth in claim 1, further comprising the step of mixing said at least one discrete substance with a second carrier gas in said interface, wherein said second carrier gas carries said at least one discrete substance through said interface and to said mass spectrometer.

3. The method for determining isotopic abundances of at least one substance in a mixture in a single continuous process as set forth in claim 2, wherein the steps of separating said first carrier gas and mixing said second carrier gas are performed simultaneously.

4. The method for determining isotopic abundances of at least one substance in a mixture in a single continuous process as set forth in claim 3, further comprising the step of mixing additional carrier gas with said at least one discrete substance and said second carrier gas before said at least one discrete substance is combusted, said additional carrier gas comprising an inert gas and oxygen, said oxygen assisting in the combustion of at least one discrete substance.

5. The method for determining isotopic abundances of at least one substance in a mixture in a single continuous process as set forth in claim 4, wherein said oxygen regenerates an oxygen source used for combustion.

6. The method for determining isotopic abundances of at least one substance in a mixture in a single continuous process as set forth in claim 2, wherein said first carrier gas is introduced at a first flowrate selected to ensure suitable gas chromatograph performance, and said second carrier gas is mixed at a second flowrate selected to ensure suitable mass spectrometer performance.

7. The method for determining isotopic abundances of at least one substance in a mixture in a single continuous process as set forth in claim 1, further comprising the step of separating water from said combustion product mixture by selectively diffusing said water through a membrane through which said combustion product mixture can not diffuse.

8. The method for determining isotopic abundances of at least one substance in a mixture in a single continuous process as set forth in claim 1, wherein a metal-oxide oxygen source is used to combust said discrete substance.

9. The method for determining isotopic abundances of at least one substance in a mixture in a single continuous process as set forth in claim 1, wherein said interface comprises a selectively permeable membrane.

10. The method for determining isotopic abundances of at least one substance in a mixture in a single continuous process as set forth in claim 9, wherein said selectively permeable membrane is selected from the group consisting of a palladium membrane, a palladium alloy membrane, and a palladium-gold alloy membrane.

11. The method for determining isotopic abundances of at least one substance in a mixture in a single continuous process as set forth in claim 9, wherein said selectively permeable membrane is a gas-cooled permeable membrane.

12. The method for determining isotopic abundances of at least one substance in a mixture in a single continuous process as set forth in claim 1, further comprising the steps of:
   introducing a further sample of known isotopic composition at a time other than the time at which the substance is being isotopically analyzed;

isotopically analyzing the further sample; and comparing the isotopic abundances of the substance and the further sample.

13. The method for determining isotopic abundances of at least one substance in a mixture in a single continuous process as set forth in claim 1, further comprising the step of separately and continuously monitoring the isotopic abundances at a plurality of isotopic masses.

14. An apparatus for measuring isotopic abundances of at least one of a plurality of substances in a mixture with a first carrier gas, comprising:

resolving means for resolving said plurality of substances mixed with said first carrier gas into at least one discrete substance mixed with said first carrier gas;

carrier gas replacement means for receiving said at least one discrete substance mixed with said first carrier gas from said resolving means and replacing said first carrier gas with a second carrier gas; and isotopic mass analyzing means for receiving and isotopically analyzing said at least one discrete substance in said second carrier gas;

wherein said carrier gas replacement means includes a selectively permeable membrane through which said first carrier gas, but not said second carrier gas and said at least one discrete substance, can diffuse.

15. The apparatus for measuring isotopic abundances as set forth in claim 14, wherein said carrier gas replacement means includes valve means for selectively diverting said first carrier gas from said resolving means away from said carrier gas replacement means by reversing the direction of flow within said carrier gas replacement means.

16. The apparatus for measuring isotopic abundances as set forth in claim 14, wherein said resolving means is a gas chromatograph and said isotopic analyzing means is a mass spectrometer.

17. The apparatus for measuring isotopic abundances as set forth in claim 14, wherein said selectively permeable membrane is selected from the group consisting of a palladium membrane, a palladium alloy membrane, and a palladium-gold alloy membrane.

18. The apparatus for measuring isotopic abundances as set forth in claim 14, wherein said selectively permeable membrane is a gas-cooled permeable membrane.

19. The apparatus for measuring isotopic abundances as set forth in claim 14, wherein said isotopic mass analyzing means is a mass spectrometer.

20. The apparatus for measuring isotopic abundances as set forth in claim 19, wherein said mass spectrometer includes means for separately and continuously monitoring the isotopic abundances at a plurality of isotopic masses.

21. The apparatus for measuring isotopic abundances as set forth in claim 14, further comprising quantitative combustion means for combusting said at least one discrete substance.

22. The apparatus for measuring isotopic abundances as set forth in claim 21, further comprising means for separating water from the other products of the combustion means.

* * * * *